(12) United States Patent
Norton et al.

(10) Patent No.: US 8,441,268 B2
(45) Date of Patent: May 14, 2013

(54) NON-CONTACT DETECTION OF SURFACE FLUID DROPLETS

(75) Inventors: Peter Norton, Berkeley, CA (US); Charley Abboud, Hayward, CA (US)

(73) Assignee: Lam Corporation, Fremont, CA (US)

( * ) Notice: Subject to any disclaimer, the term of this patent is extended or adjusted under 35 U.S.C. 154(b) by 486 days.

(21) Appl. No.: 12/755,090

(22) Filed: Apr. 6, 2010

(65) Prior Publication Data

US 2011/0241706 A1 Oct. 6, 2011

(51) Int. Cl.
*G01R 27/26* (2006.01)

(52) U.S. Cl.
USPC ........... 324/686; 324/658; 324/661; 324/687; 73/514.32; 73/862.22; 73/862.52; 702/52

(58) Field of Classification Search .............. 324/658, 324/686, 661, 687, 689–694; 73/780, 514.32, 73/862.22, 862.52; 702/52
See application file for complete search history.

(56) References Cited

U.S. PATENT DOCUMENTS

| | | | |
|---|---|---|---|
| 5,038,110 A * | 8/1991 | Braun et al. | 324/675 |
| 5,734,164 A * | 3/1998 | Sanford | 250/310 |
| 5,801,307 A * | 9/1998 | Netzer | 73/170.17 |
| 6,373,263 B1 * | 4/2002 | Netzer | 324/665 |
| 6,392,745 B1 | 5/2002 | Mavliev et al. | |
| 6,452,514 B1 | 9/2002 | Philipp | |
| 6,764,168 B1 | 7/2004 | Meinhold et al. | |
| 6,789,426 B2 * | 9/2004 | Yaralioglu et al. | 73/597 |
| 6,848,194 B2 * | 2/2005 | Treur | 34/58 |
| 7,116,117 B2 | 10/2006 | Nakano et al. | |
| 7,508,221 B2 * | 3/2009 | Wuersch et al. | 324/663 |
| 2007/0247165 A1 | 10/2007 | Herchen | |
| 2007/0297631 A1 * | 12/2007 | Miles | 381/369 |
| 2008/0217530 A1 | 9/2008 | Hawthorne et al. | |
| 2009/0181475 A1 * | 7/2009 | Akasako | 438/5 |
| 2011/0043224 A1 * | 2/2011 | Yu et al. | 324/658 |
| 2012/0062251 A1 * | 3/2012 | Gonzalez et al. | 324/686 |
| 2012/0154324 A1 * | 6/2012 | Wright et al. | 345/174 |

OTHER PUBLICATIONS

M. Shahrooz Amin et al; Measurements of electric charge associated with evaporation and condensation of water on metallic surfaces as a consequence of pressure, Journal of Electrostatics 64 (2006) 597-603.

P.A. Sorichetti et al; "Low-frequency dielectric measurements of complex fluids using high-frequency coaxial sample cells", P.A. Sorichetti, C.L. Matteo, Department of Physics, Faculty of Engineering, University of Buenos Aires, Measurement 40 (2007) 437-449.

Victor Kremin et al; "Application Note AN2398 Capacitance Sensing, Waterproof Capacitance Sensing", Cypress Semiconductor Inc., Dec. 8, 2006.

(Continued)

*Primary Examiner* — Huy Q Phan
*Assistant Examiner* — Thang Le
(74) *Attorney, Agent, or Firm* — Klintworth & Rozenblat IP LLC

(57) ABSTRACT

A system for detecting fluid on a substrate is provided. The system includes, but is not limited to, a sensor board, a first capacitive sensor, and a platform upon which the substrate is to be placed. The first capacitive sensor is mounted on the sensor board. The first capacitive sensor has a transmit sensor pad for transmitting a signal, a receive sensor pad for receiving the signal, and an analog-to-digital convertor connected with the receive sensor pad for analyzing the received signal. The platform is a first distance from the transmit and receive sensor pads.

20 Claims, 17 Drawing Sheets

OTHER PUBLICATIONS

William P. Winn; "An Electrostatic Theory for Instruments which Measure the Radii of Water Drops by Detecting a Change in Capacity Due to the Presence of a Drop", William P. Winn, Journal of Applied Meteorology, 1968, Abstract.

Korean Intellectual Property Office (International Searching Authority) The International Search Report and the Written Opinion for PCT/US2011/030262, Date of Mailing Nov. 30, 2011.

* cited by examiner

NON-CONTACT DETECTION OF SURFACE FLUID DROPLETS

FIELD OF THE INVENTION

The present invention relates to detection of surface fluid droplets. More specifically, it relates to a method and device for non-contact detection of surface fluid droplets formed on a substrate.

BACKGROUND

Traditionally, upon or during the fabrication process, semiconductor substrates are often cleaned via a cleaning process. When a semiconductor substrate has been through a cleaning process, wherein chemicals such as dilute hydrofluoric acid, or isopropyl alcohol, or deionized water are applied to the semiconductor substrate and subsequently rinsed off the semiconductor substrate, droplets of fluid may remain on the semiconductor substrate.

If fluid droplets are left on a semiconductor substrate as it exits a cleaning process, the fluid droplets may cause problems in further semiconductor fabrication processing steps and may lead to the semiconductor substrate being destroyed. Therefore, it is critical to be able to detect the presence of fluid droplets, such as droplets of deionized water, isopropyl alcohol, or other fluids left on the semiconductor substrate, before the semiconductor substrate enters a further stage of processing, and before the fluid droplets have had a chance to evaporate in air leaving a residue.

Currently, there are a few methods employed for non-contact detection of fluid droplets formed on a surface of a semiconductor substrate. One method uses video from a camera, digitizes the video using a dedicated computer, and then subjects the video to image processing to detect images of fluid droplet on the surface of the semiconductor substrate. One method shines a laser on the surface of the semiconductor substrate at a grazing incidence, and then uses a charged-coupled device (CCD) optical detector to detect laser light scattering off the fluid droplets. These methods are relatively expensive to implement, require expensive optics and careful calibration, are subject to false alarms and missed detection of fluid droplets.

It would be desirable to have a less expensive and more reliable method and device for non-contact detection of surface fluid droplets formed on a substrate.

SUMMARY

In one aspect, a system for detecting fluid on a substrate is provided. The system includes, but is not limited to, a sensor board, a first capacitive sensor, and a platform upon which the substrate is to be placed. The first capacitive sensor is mounted on the sensor board. The first capacitive sensor has a transmit sensor pad for transmitting a signal, a receive sensor pad for receiving the signal, and an analog-to-digital convertor connected with the receive sensor pad for analyzing the received signal. The platform is a first distance from the transmit and receive sensor pads.

In one aspect, a method for detection of fluid on a substrate is provided. The method includes, but is not limited to, placing a substrate on a platform under a fluid detector. The fluid detector comprises a sensor board and a first capacitive sensor mounted on the sensor board. The method also includes but is not limited to measuring the capacitance of the capacitive sensor and determining if fluid is on the substrate based on the measured capacitance of the capacitive sensor.

In one aspect, an apparatus for detecting fluid on a substrate is provided. The apparatus includes, but is not limited to, a first capacitive sensor positioned a distance away from a platform upon which the substrate is to be placed. The first capacitive sensor has a transmit sensor pad for transmitting a capacitance signal, a receive sensor pad for receiving the capacitance signal, and an analog-to-digital convertor connected with the receive sensor pad for analyzing the received capacitance signal and determining any change in capacitance of the first capacitive sensor. The capacitive sensor is capable of forming an electric field between the transmit sensor pad and the receive sensor pad when transmitting the capacitance signal. The electric field is capable of traveling to a surface of a substrate on the platform. The apparatus also includes, but is not limited to, detection circuitry connected with the analog-to-digital convertor, comprising a microprocessor executing pattern recognition and decision making algorithms. The detection circuitry is for analyzing any change in capacitance of the first capacitive sensor by determining any change in the electric field, and then determining if any fluid is present on a surface of a substrate on the platform.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that by placing a non-contact capacitive sensor near a substrate, and then by moving the substrate across the capacitive sensor, is possible to detect fluid droplets on the substrate reliably and cost effectively.

Figure 1:
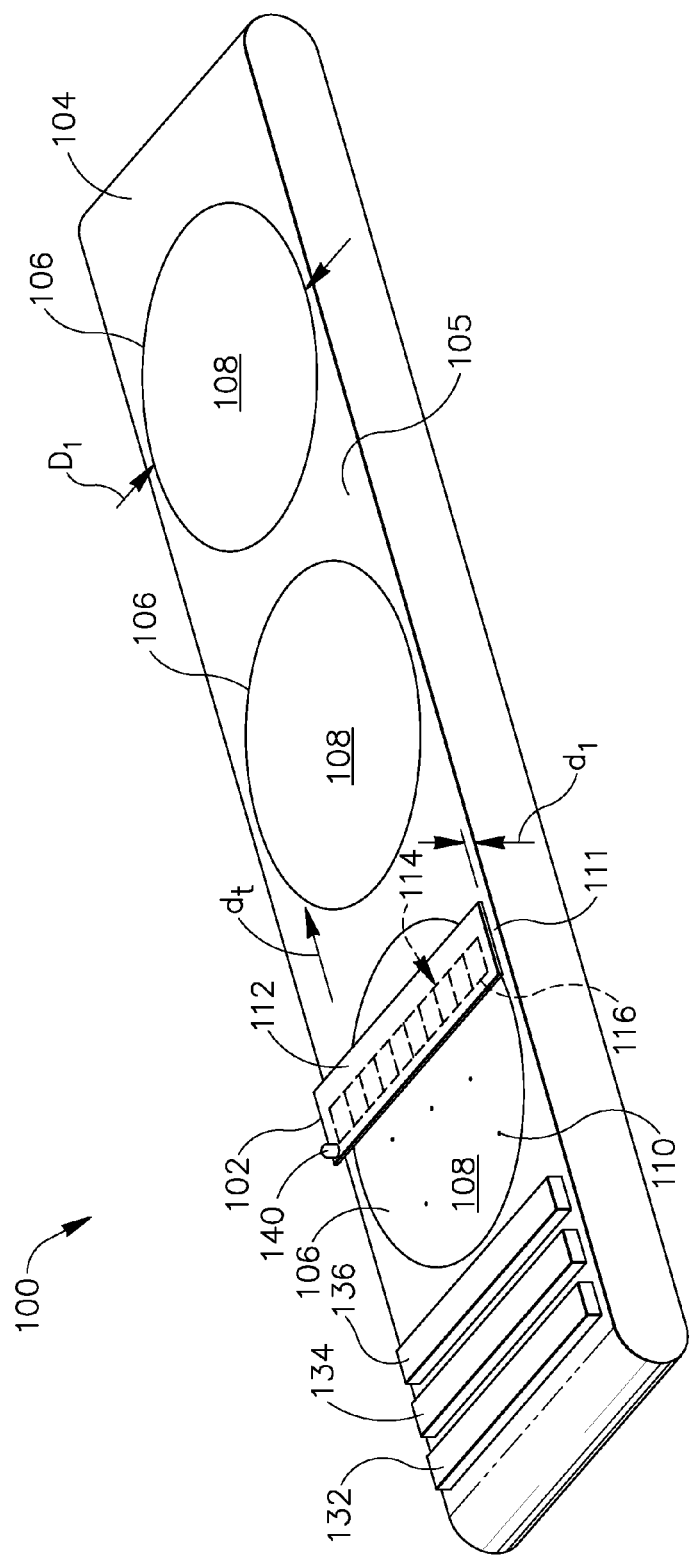
FIG. 1 depicts a perspective view of a system for detecting fluid on a substrate, in accordance with one embodiment of the present invention.
Figure 2:
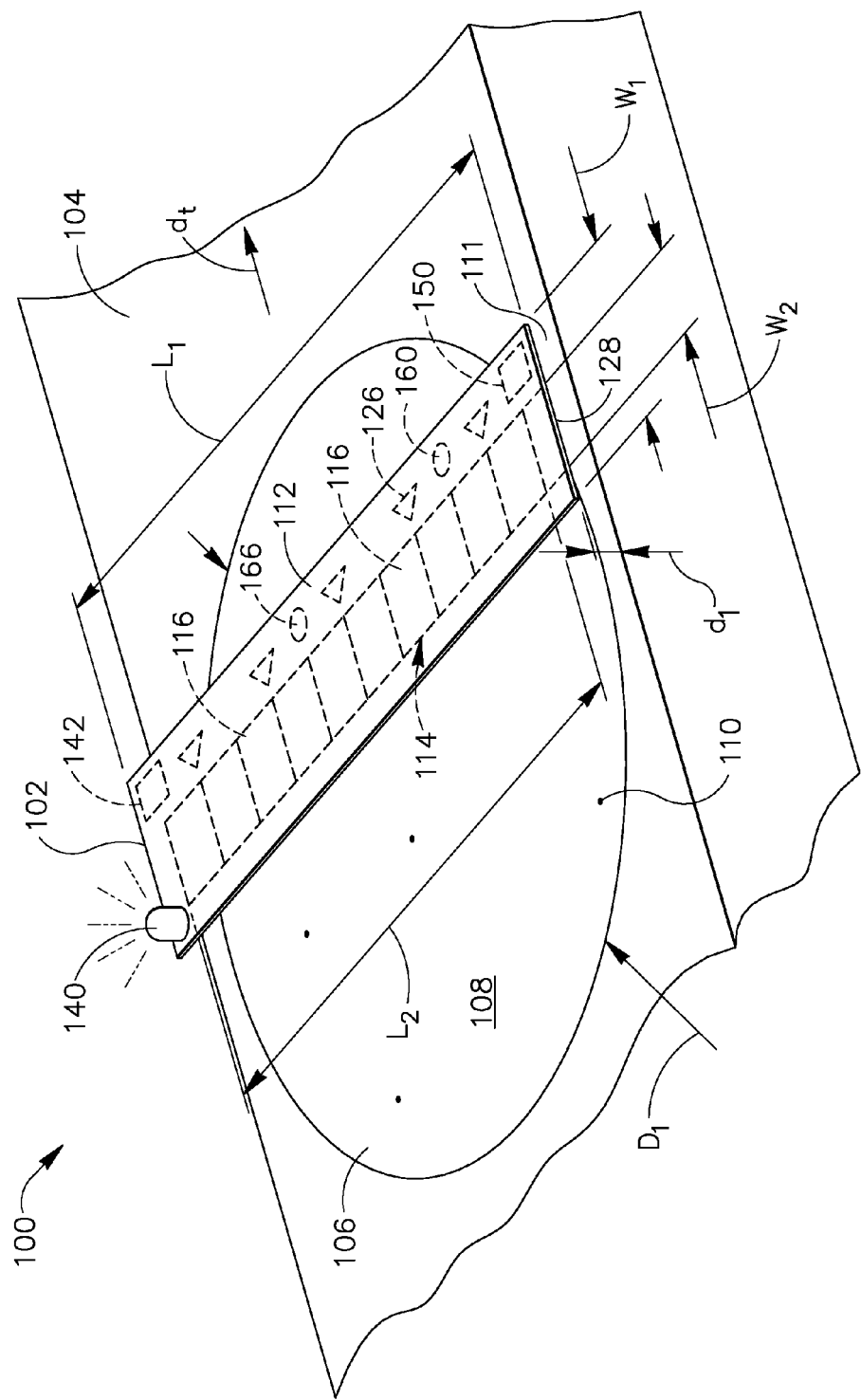
FIG. 2 depicts an enlarged perspective view of the system for detecting fluid on a substrate shown in FIG. 1, in accordance with one embodiment of the present invention.

Referring to FIGS. 1 and 2, there is shown a system 100 for detecting fluid 110 on a substrate 106. Fluid 110 includes any fluid which may form or be deposited on the surface of a substrate, such as water, deionized water, isopropyl alcohol, any cleaning fluid, or any polishing fluid. The fluid may cover a substantial fraction of the wafer ('flooding' the wafer) or form into droplets. The detection method described accommodates either the flooding or droplet situations. Preferably, the fluid 110 forms into droplets having a diameter of at least 0.1 millimeters, more preferably of at least 1.0 millimeters, and most preferably from 0.1 millimeters to 5.0 millimeters. Preferably, the droplets of fluid 110 have a volume of at least 1 microliter, more preferably at least 10 microliters, and most preferably from 1 microliter to 1000 microliters.

Substrate 106 includes any one of a variety of disc-shaped or non-disc-shaped substrates, such as: silicon based substrates including glass, dry glass, semiconductor wafers, flat panel display glass panels, glass production panels, and printed circuit boards; polymer-based substrates; and various types of semiconductor substrates, such as silicon-based semiconductor substrates, single element semiconductor substrates, silicon on insulator (SOI) substrates, III-V semiconductor substrates, II-VI semiconductor substrates, other binary semiconductor substrates, ternary semiconductor substrates, quaternary semiconductor substrates; fiber optic substrates; superconducting substrates; glass substrates; fused quartz substrates; fused silica substrates; epitaxial silicon substrates; and organic semiconductor substrates.

Figure 3:
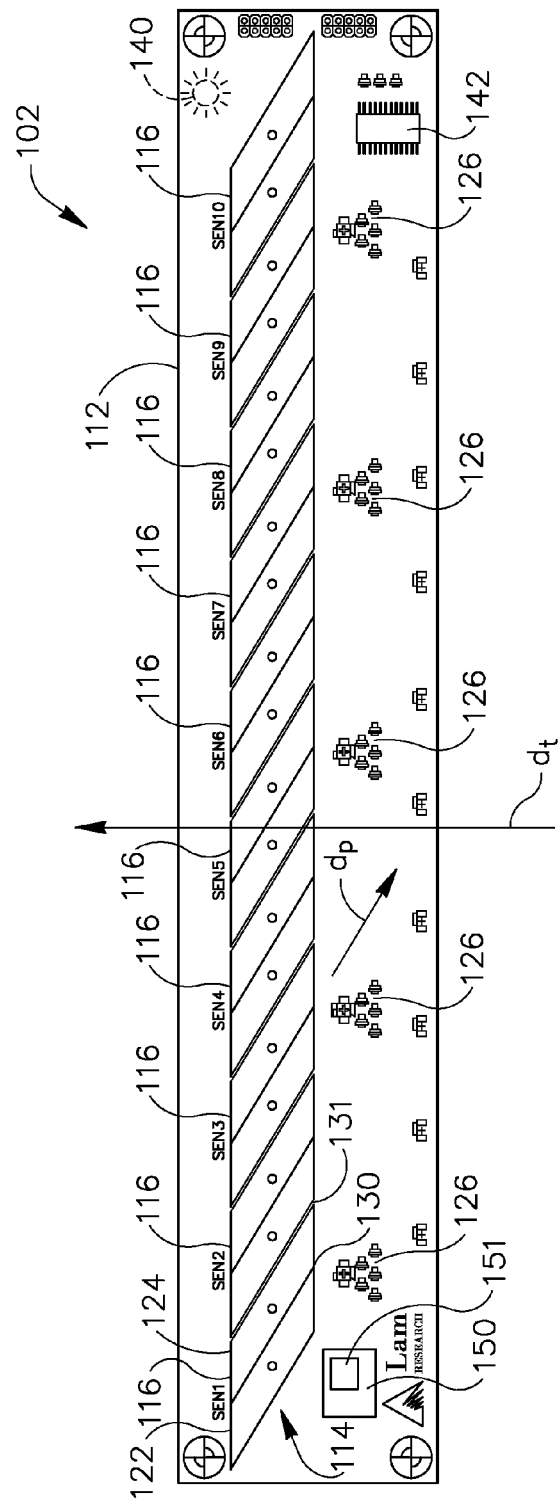
FIG. 3 depicts a bottom view of a fluid detector from a system for detecting fluid on a substrate, in accordance with one embodiment of the present invention.
Figure 4:
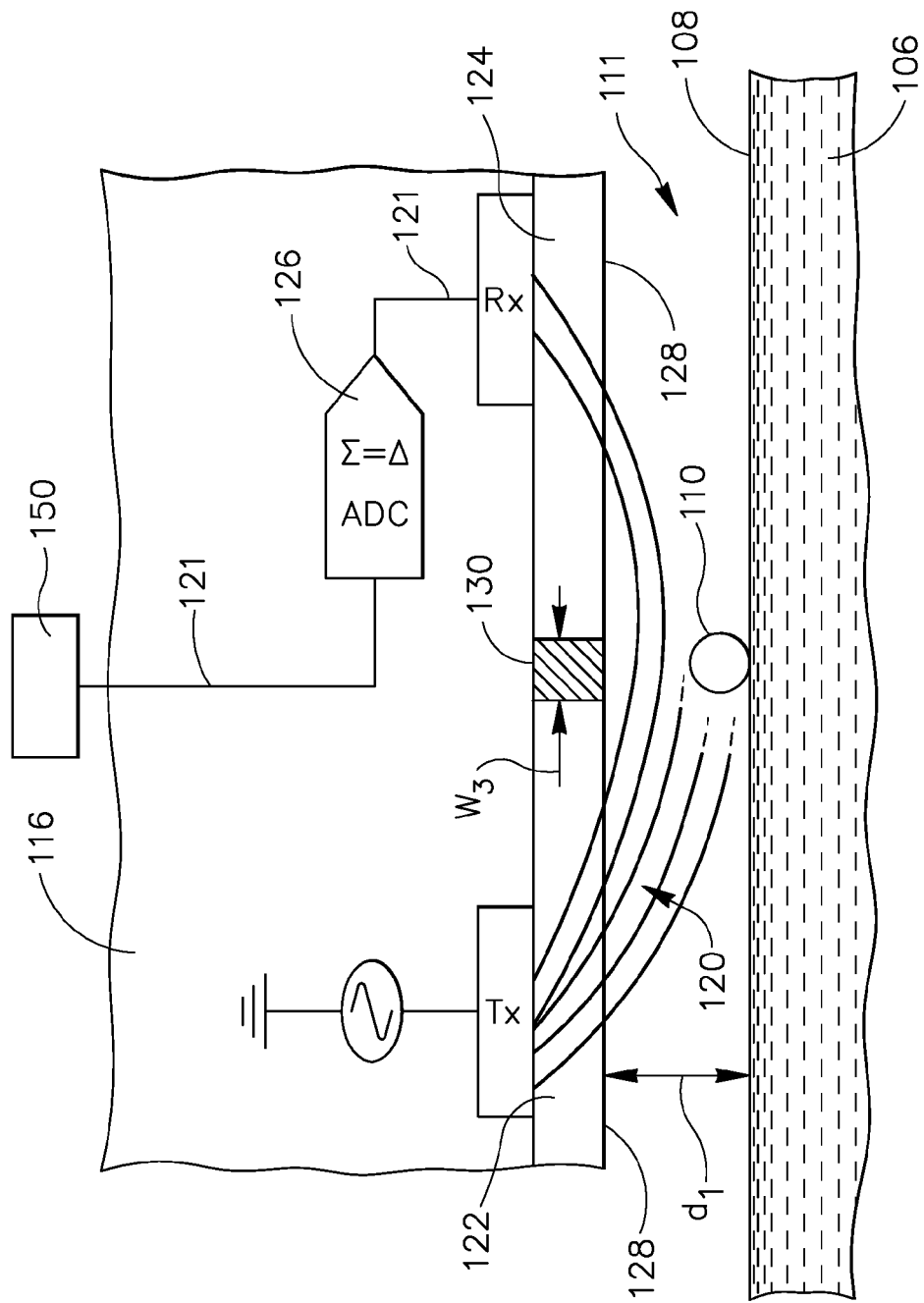
FIG. 4 depicts an enlarged partial cross-sectional view a fluid detector from a system for detecting fluid on a substrate, in accordance with one embodiment of the present invention.
Figure 5:
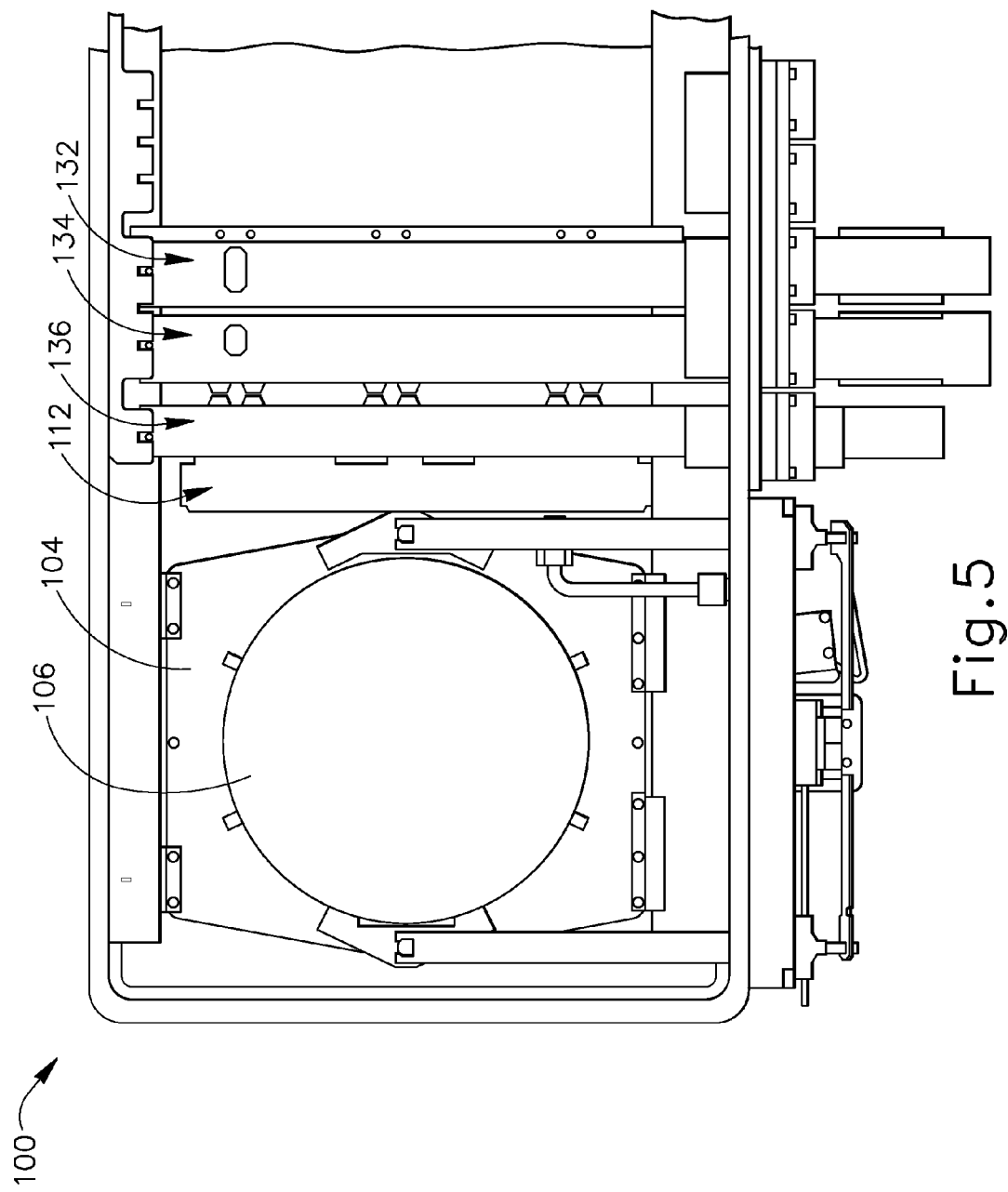
FIG. 5 depicts a top view of a system for detecting fluid on a substrate, in accordance with one embodiment of the present invention.
Figure 6:
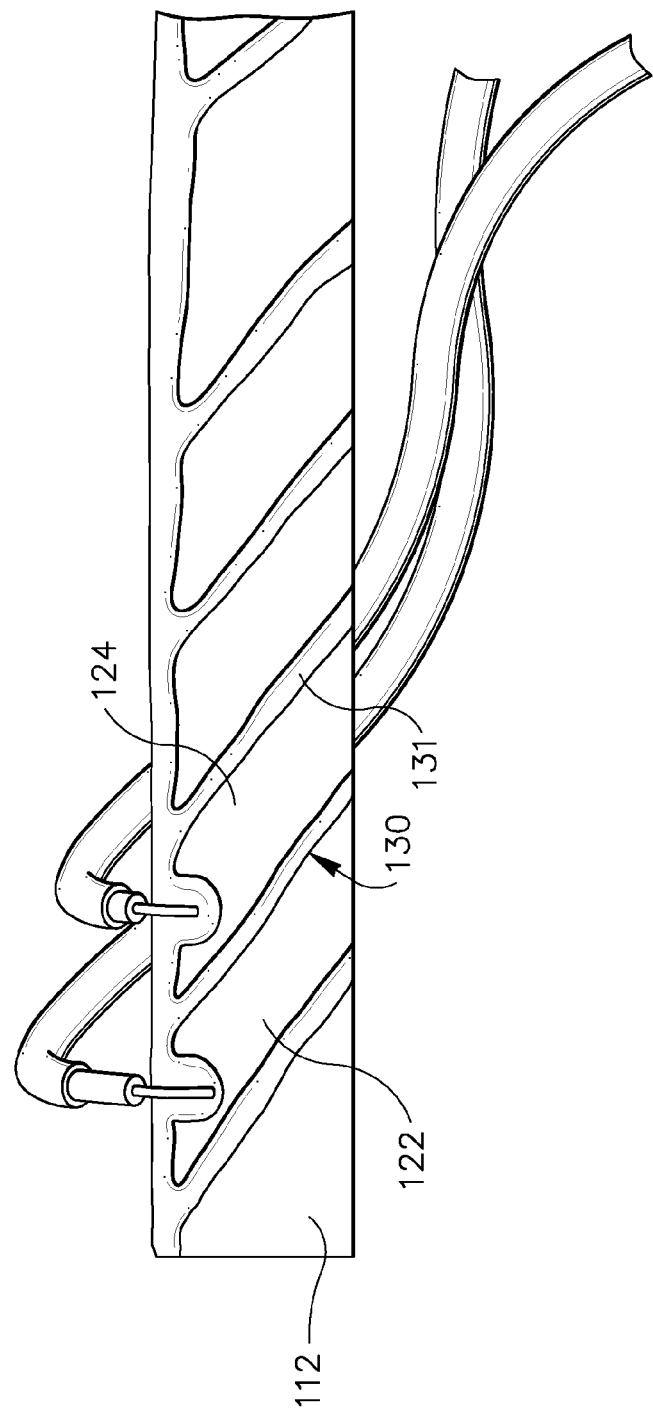
FIG. 6 depicts a bottom view of a fluid detector from a system for detecting fluid on a substrate, in accordance with one embodiment of the present invention.
Figure 11:
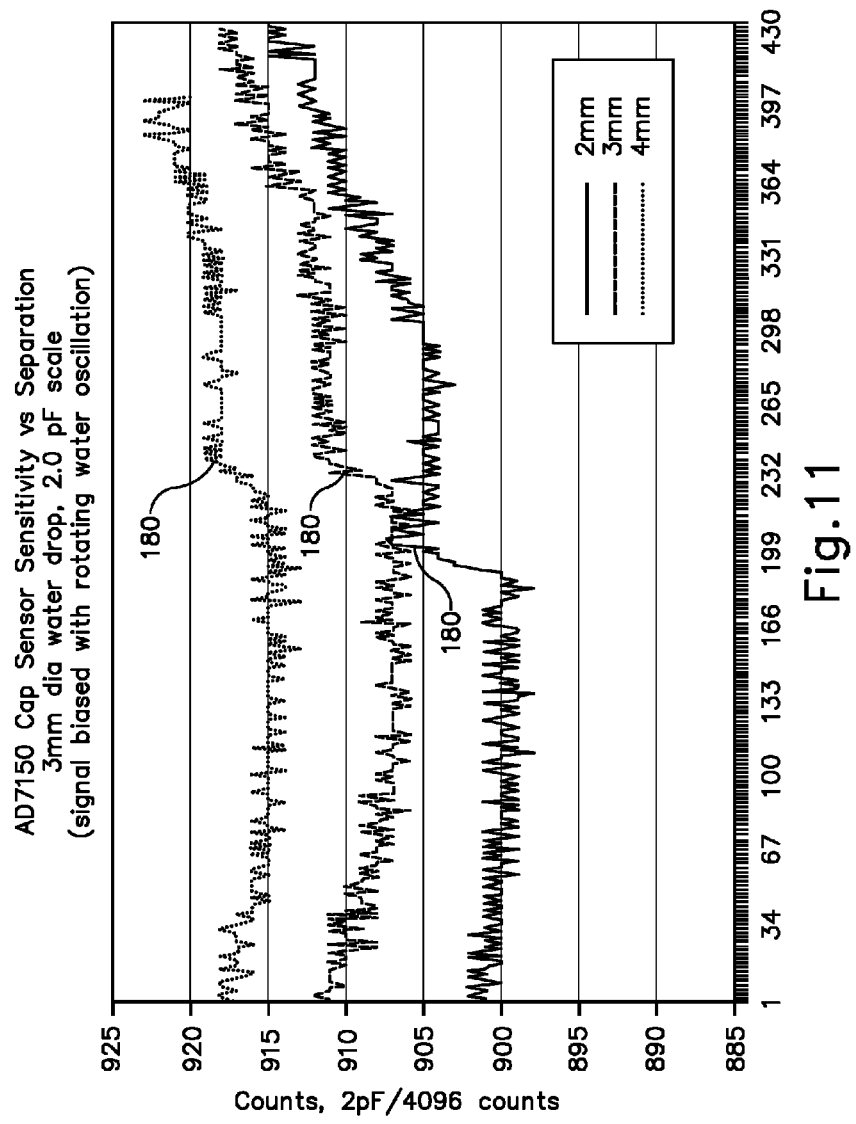
FIGS. 11-12 depict charts graphing response data received from a capacitive sensor of a fluid detector against a distance $d_1$ from the capacitive sensor to a surface of a substrate for various sizes of fluid droplets, in accordance with one embodiment of the present invention.
Figure 12:
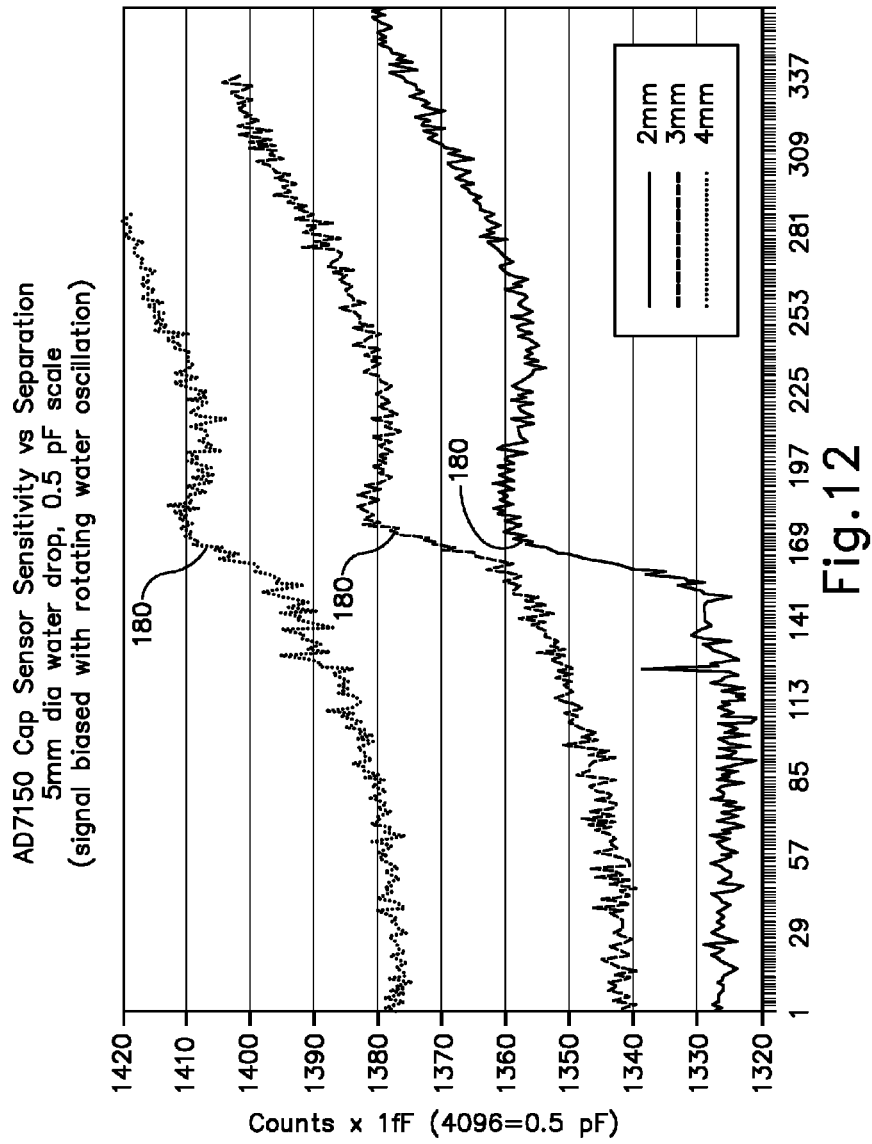

Referring to FIGS. 2, 3, and 4, system 100 includes a fluid detector 102 having a capacitive sensor 116 positioned a distance $d_1$ away from a platform 104 upon which the substrate 106 is to be placed, and detection circuitry 150 connected with the capacitive sensor 116. The distance $d_1$ is preferably as close as possible to the surface 105, without touching the substrate 106. Preferably, the distance $d_1$ is 10 mm or less, more preferably from 0.1 mm to 5 mm, and most preferably from 1 mm to 4 mm. As shown in FIGS. 11 and 12, as the distance $d_1$ moves from 2 mm to 3 mm, and then from 3 mm to 4 mm, the detection of a droplet of fluid 110 using capacitive sensor 116, as represented by spike 180, becomes more difficult as the spike 180 becomes smaller.

Figure 7:
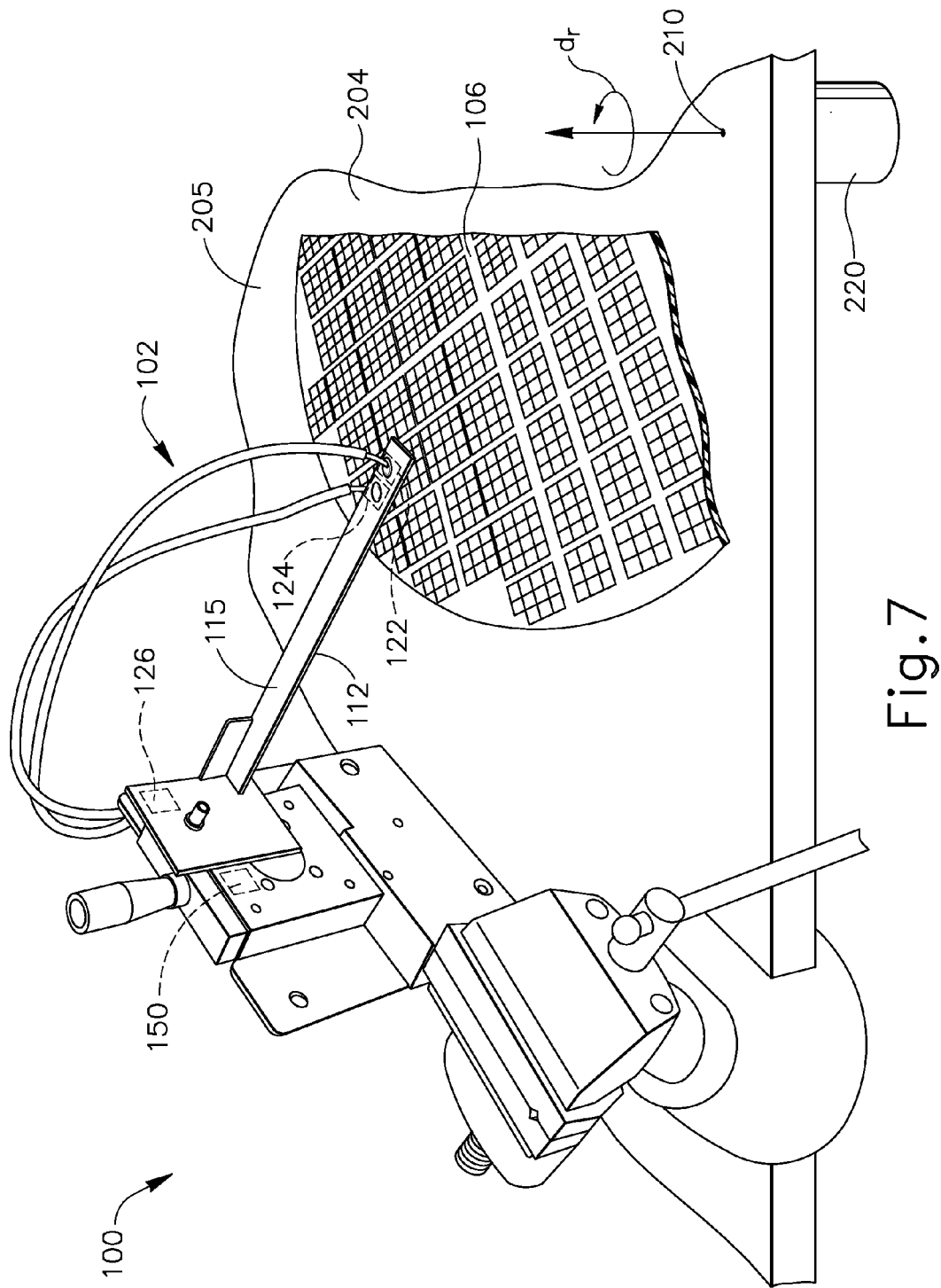
FIG. 7 depicts a perspective view of a system for detecting fluid on a substrate, in accordance with one embodiment of the present invention.

Platform 104 provides a mounting surface 105 upon which substrates 106 are placed. Preferably, the mounting surface 105 is generally level with the ground, providing substrates 106 with a generally level surface upon which to rest. Platform 104 is located a distance $d_1$ beneath a bottom surface 128 of the fluid detector 102, and more specifically the capacitive sensor 116. Preferably, the platform 104 is a conveyor system, which can move substrates 106 either linearly or rotationally under the fluid detector 102. FIGS. 1 and 2 illustrate a platform 104 which is a conveyor system capable of moving substrates 106 in a linear direction of travel $d_t$ underneath fluid detector 102. Preferably, the platform 104 is located underneath a chemical head 132 which applies chemicals to the substrate 106, is located underneath a rinse head 134 for rinsing off and removing the chemicals applied, and is located underneath an exit head 136 used to dry the wafer by means of vacuum suction. Referring to FIG. 7, a platform 204 having a circular mounting surface 205 is provided. The platform 204 is generally round and rotates in a direction $d_r$ about a centralized axis 210 normal with the mounting surface 205. The platform 204 is connected with a rotational device 220 for rotating the platform 204 about the centralized axis 210.

Capacitive sensor 116 includes any type of sensor which measures variations in capacitance. Preferably, capacitive sensor 116 is a noncontact capacitive sensor which works by measuring changes in capacitance. Preferably, capacitive sensor 116 uses an alternating voltage which causes charges on the sensor 116 to continually reverse their positions. The moving of the charges creates an alternating electric current which is detected by the capacitive sensor 116. The amount of current flow is determined by the capacitance, and the capacitance is determined by the area, proximity, and relative dielectric constant, of nearby objects, such as fluid 110. Larger and closer objects cause greater current than smaller and more distant objects. The capacitance of capacitive sensor 116 is also affected by the type of nonconductive material in an air gap 111 between the capacitive sensor 116 and objects such as fluid 110.

Preferably, capacitive sensor 116 is sensitive enough to detect a change in capacitance from the presence of a droplet of fluid 110 on a surface 108 of substrate 106, such as a droplet of deionized water, preferably having a volume of at least 1 microliter, more preferably a volume of at least 10 microliters, and most preferably a volume from 1 microliter to 1000 microliters. Preferably, the capacitive sensor 116 can detect and measure a change in capacitance of 100 pico-Farads or less, more preferably a change in capacitance of 100 femto-Farads or less, and most preferably a change in capacitance of 5 femto-Farads or less, all preferably with a resolution of ten, and more preferably, five, femto-Farads or less. In one embodiment, capacitive sensor 116 is a model AD7147 Captouch capacitance-to-digital converter capacitive sensor manufactured by Analog Devices, Inc. of Norwood, Mass. In one embodiment, capacitive sensor 116 is a model AD7150 ultra-low power, 2-channel, capacitance converter for proximity sensing manufactured by Analog Devices, Inc. of Norwood, Mass.

Each capacitive sensor 116 includes a transmit sensor pad 122 for transmitting a capacitance signal 121, a receive sensor pad 124 for receiving the capacitance signal 121, and an analog-to-digital convertor 126 connected with the receive sensor pad 124 for analyzing the received capacitance signal 121 and determining any change in capacitance of the capacitive sensor 116. Sensor pads 122 and 124 are mounted a distance $d_1$ above the platform 104, and more specifically, above the surface 105 of the platform 104, with the sensor pads 122 and 124 facing the platform 104, as shown in FIG. 2. Preferably, sensor pads 122 and 124 comprise a conductive material, such as a metal.

The transmission of the capacitance signal 121 from the transmit sensor pad 122 to the receive sensor pad 124 generates an electric field 120. If the electric field 120 is interrupted by a certain sized object, such as a droplet of fluid 110, the value of the received capacitance signal 121 is altered, and the overall capacitance of the capacitive sensor 116 is measurably changed. Upon receipt of the capacitance signal 121 by the receive sensor pad 124, the capacitance signal 121 is converted from analog form to digital form via the analog-to-digital convertor 126 and then transmitted to the detection circuitry 150 for analyses.

In one embodiment, the fluid detector 102 includes a substrate presence detector 160 and a substrate travel speed detector 164. The substrate presence detector 160 is any type of device or combination of devices which can detect the presence of substrate 106, and may include devices such as a laser beam or an optical scanner. Upon detection of substrate 106, the substrate presence detector 160 generates a substrate presence signal which is then received and analyzed by the detection circuitry 150. The substrate travel speed detector 164 is any type of device or combination of devices which can determine the velocity of the substrate 106 traveling down the platform 104, and may include a laser beam, an optical scanner, or a radio frequency wave. Upon determination of the velocity of the substrate 106, the substrate travel speed detector 164 generates a substrate travel speed signal which is then received and analyzed by the detection circuitry 150.

The detection circuitry 150 is connected with the analog-to-digital convertor 126 and comprises a microprocessor 152 executing pattern recognition and decision making algorithms. The detection circuitry 150 analyzes any change in capacitance of the first capacitive sensor 116 by determining any change in the electric field 120, and then determining if any fluid 110 is present on surface 108 of substrate 106 on the platform 104. The detection circuitry 150 analyzes any change in capacitance, and specifically, any change in the capacitance signal 121, in order to determine if fluid 110 is present on the surface 108 of substrate 106 on the platform 104.

Figure 13:
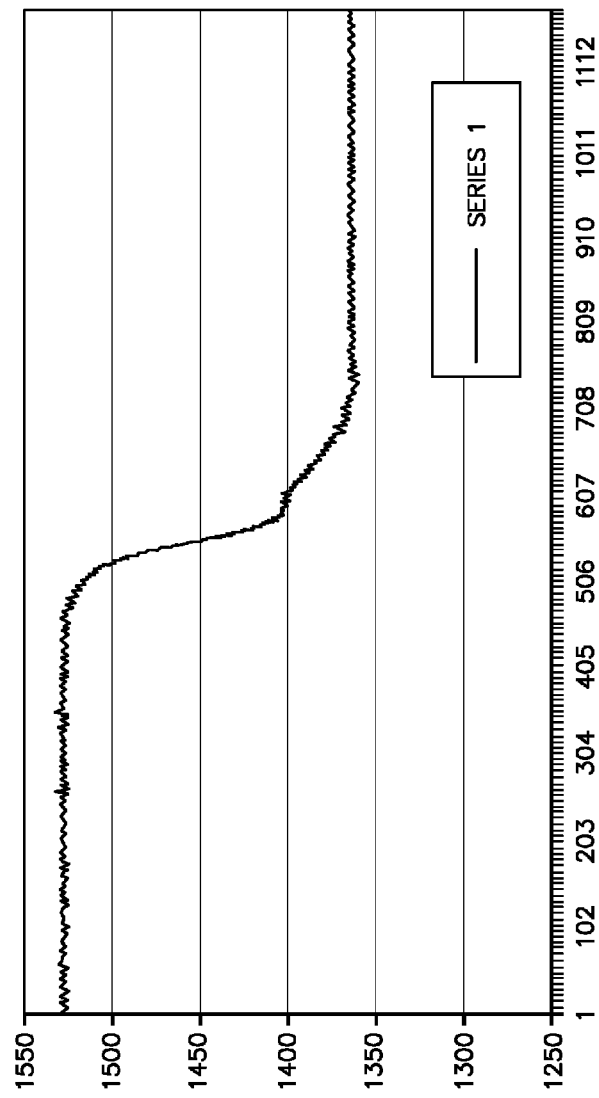
FIG. 13 depicts a chart graphing response data received from a capacitive sensor of a fluid detector when passing an edge of a substrate, in accordance with one embodiment of the present invention.
Figure 14A:
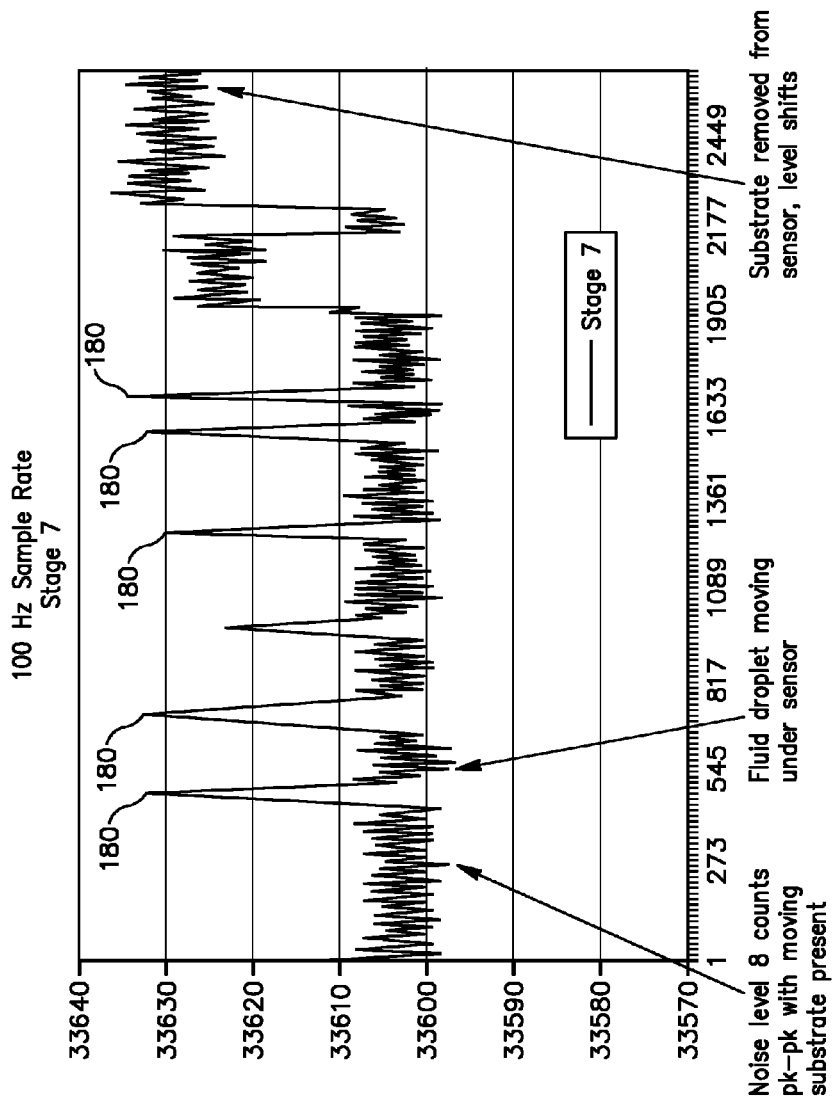
FIG. 14A depicts a chart graphing response data received from a capacitive sensor of a fluid detector with fluid droplets of 4 mm in diameter at a distance $d_1$ of 4 mm and at a 100 Hz sample rate, in accordance with one embodiment of the present invention.

In one embodiment, the detection circuitry 150 receives the capacitance signal 121 from the analog-to-digital convertor 126, along with a substrate presence signal from the substrate presence detector 160, and a substrate travel speed signal from the substrate travel speed detector 164. Using pattern recognition and decision making algorithms, the detection circuitry 150 then determines, based upon the value of the capacitance signal 121, the substrate presence signal, and the substrate travel speed signal, whether fluid 110 is present on the substrate 106. The detection circuitry 150 makes this determination in the following manner. First, the detection circuitry 150 determines if a substrate 106 is present a distance $d_1$ or less away from the sensor pads 118 of the capacitive sensor 116 by analyzing the value of the substrate presence signal, or by analyzing the values of the capacitance signal 121 for substantial changes, as shown in FIGS. 13 and 14A. If the detection circuitry 150 determines that a substrate 106 is present, the detection circuitry 150 then determines the speed of that substrate 106 by analyzing the value of the substrate travel speed signal, or by analyzing the values of the capacitance signal 121 for substantial changes indicating an edge of a substrate 106, as shown in FIGS. 13 and 14A.

Figure 8:
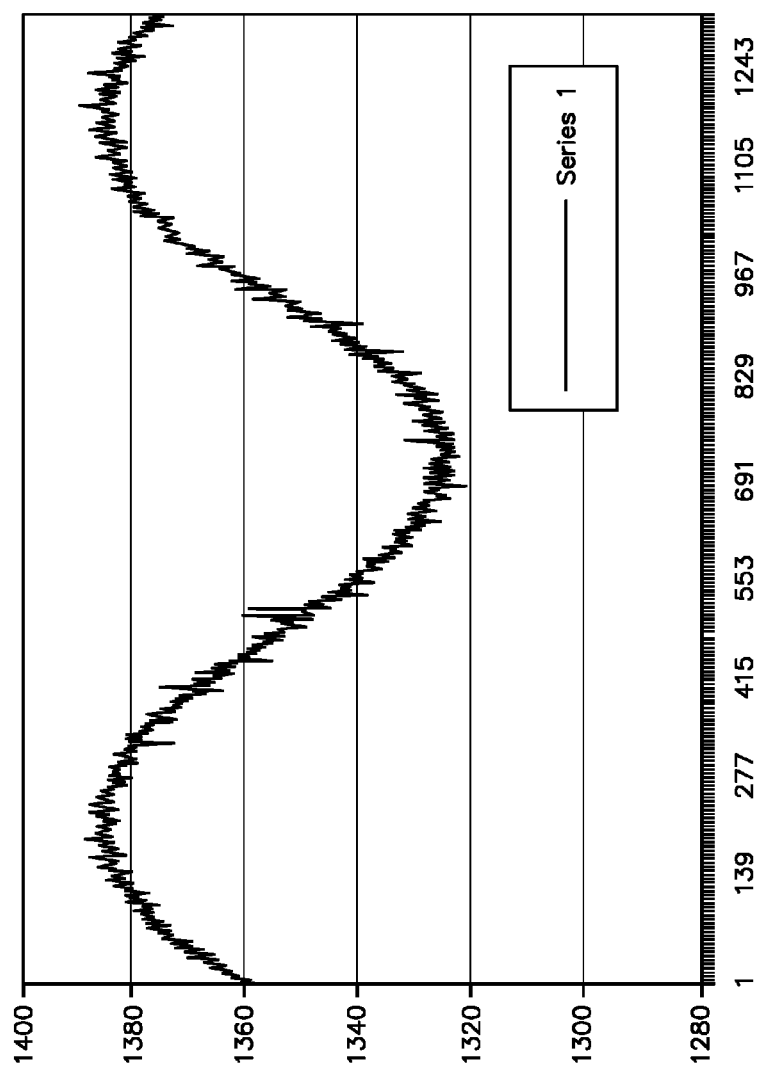
FIGS. 8-10 depict charts graphing response data received from a capacitive sensor of a fluid detector, in accordance with one embodiment of the present invention.
Figure 9:
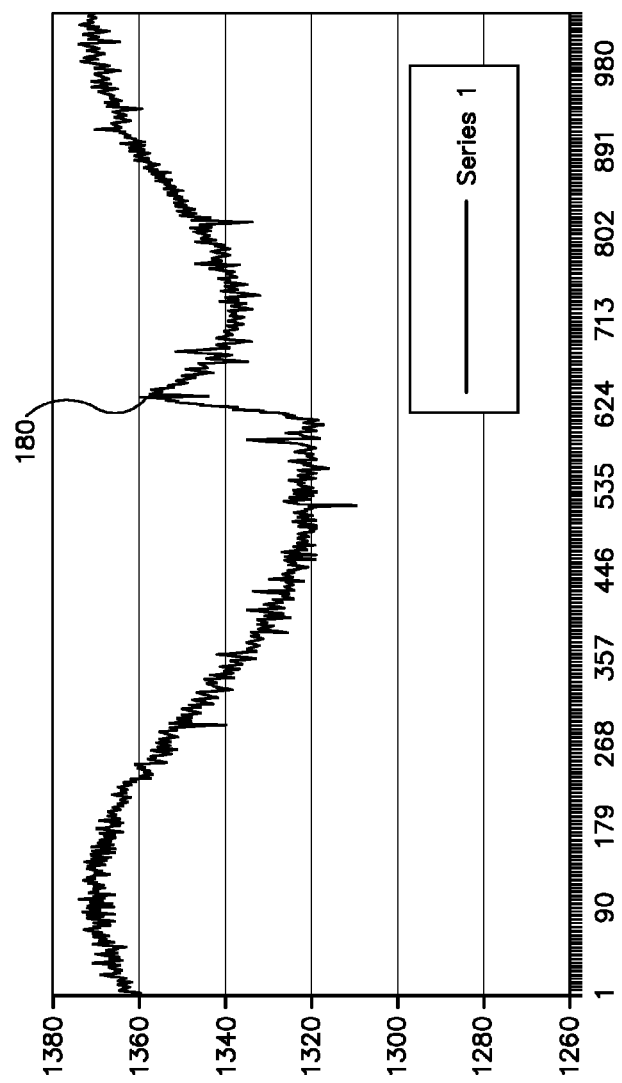
Figure 10:
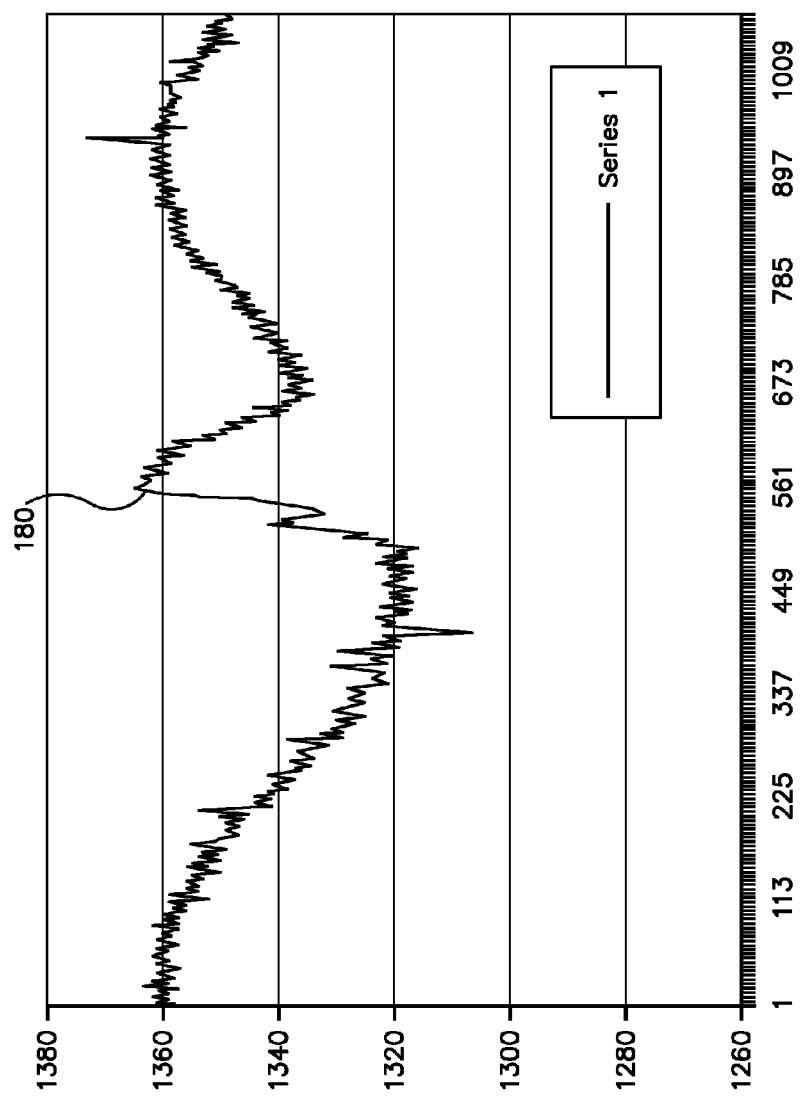

Then, using the determined speed of the substrate 106 in combination with the value of the capacitance signal 121, the detection circuitry 150 determines whether there is a sudden change or spike 180 in the capacitance signal 121 indicating that fluid 110 is on the surface 108 of substrate 106. Referring to FIGS. 9-12, a spike 180 represents a sudden change in the capacitance signal 121, beyond what the capacitance signal 121 would normally look like. For example, FIG. 8. illustrates a normal capacitance signal 121 of a wobbling, rotating substrate 106, while FIGS. 9 and 10 show the same wobbling substrate 106 with a droplet of fluid 110 represented by spike 180. Spike 180 indicates that a droplet of fluid 110 is present on the surface 108 of substrate 106. If detection circuitry 150 determines that a droplet of fluid 110 is present on the surface 108 of substrate 106, then a signal indicating that a droplet of fluid 110 is present is transmitted to an indicator 140 which communicates this information to an end user by issuing an alert. Indicator 140 is preferably part of fluid detector 102 and is connected with detection circuitry 150. Indicator 140 includes any device which can signal a user, such as an illuminating device, a speaker, a display, and a vibrating or moving device.

Figure 14B:
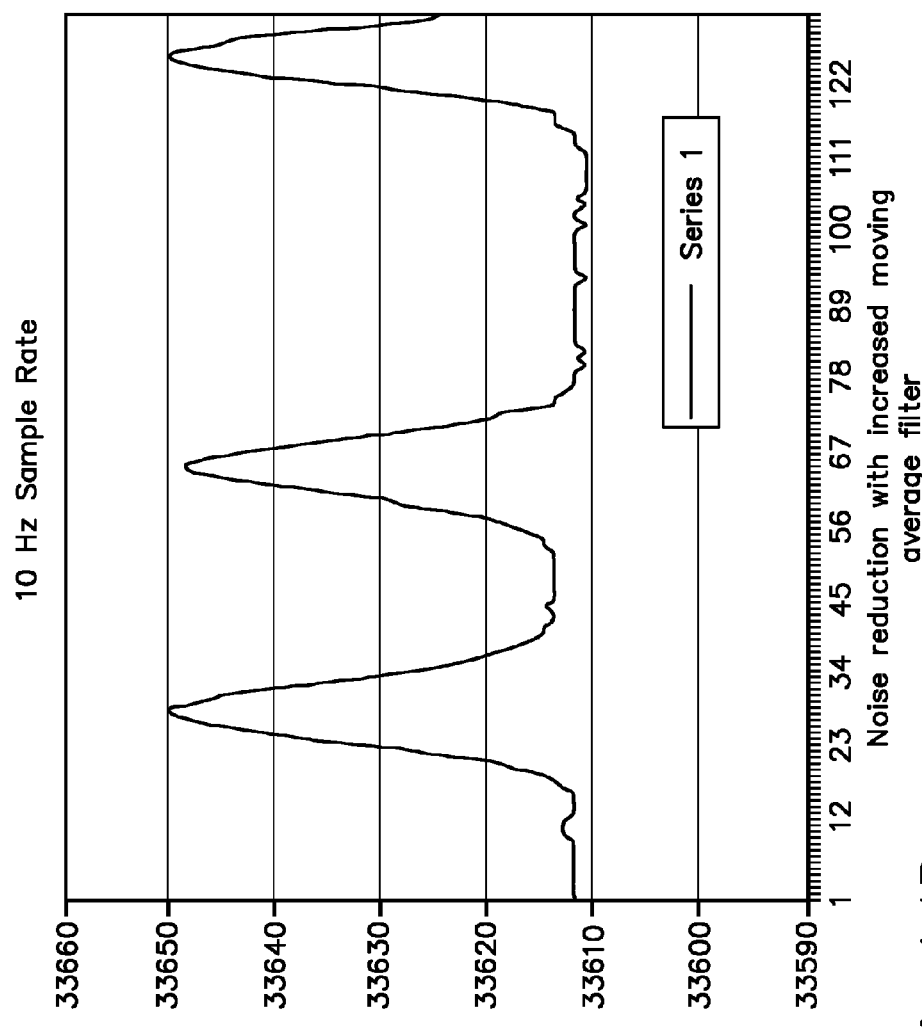
FIG. 14B depicts a chart graphing response data received from a capacitive sensor of a fluid detector with fluid droplets of 4 mm in diameter at a distance $d_1$ of 4 mm and at a 10 Hz sample rate with noise reduction applied, in accordance with one embodiment of the present invention.

Preferably, the detection circuitry 150 includes a noise-reduction algorithm which is able to reduce the peaks and valleys in capacitance signal 121 such that the presence of fluids 110 is more easily detected, as shown in FIG. 14B.

In one embodiment, the substrate presence signal is derived by the detection circuitry 150 from the capacitance signal 121 using pattern recognition algorithms. In this embodiment, the substrate presence signal is derived by analyzing a change in the capacitance signal 121, as shown in FIGS. 13 and 14A. If the change in the capacitance signal 121 is great enough, a substrate 106 has either been placed near the sensor pads 118, or has been taken away from the sensor pads 118. A large change in the capacitance signal 121 may indicate the presence or absence of substrate 106. For example, in FIG. 13, as the capacitance shifts from a level of about 1525 to a level of about 1360, this large shift in capacitance indicates that an edge of the substrate 106 has been reached. Since such a large shift in capacitance occurs at the edge of substrate 106, preferably, a pattern of the capacitance values at the edge of a substrate 106 is stored in memory so that a droplet of fluid 110 can be detected at an edge of a substrate 106. Additionally, with reference to FIG. 14A, a removal of a substrate 106 from platform 104 causes the capacitance to shift from a level of about 33605 to a level of about 33630.

In one embodiment, the substrate travel speed signal is derived by the detection circuitry 150 from the capacitance signal 121 using pattern recognition algorithms. In this embodiment, the substrate travel speed signal is generated by analyses of the time between detection of a leading edge of the substrate 106, and a trailing edge of the substrate 106, by substrate presence detector 160 in order to determine the speed of the substrate 106. A large change in the capacitance signal 121 may indicate a leading or a trailing edge of a substrate 106.

In one embodiment, the fluid detector 102 includes a sensor board 112 for mounting components such as capacitive sensor 116, detection circuitry 150, indicator 140, multiplexor 142, detection circuitry 150, substrate presence detector 160, and substrate travel speed detector 166. The sensor board 112 is a rigid platform on which components such as the capacitive sensors 116 are mounted. Preferably, the sensor board 112 has a width $W_1$ greater than a width $W_2$ of the capacitive sensors 116 and a length $L_1$ greater than half a width or half a diameter $D_1$ of the substrates 106. In one embodiment, the sensor board 112 has a length $L_1$ greater than the width or the diameter $D_1$ of the substrates 106. In this manner, the sensor board 112 can mount an array 114 of capacitive sensors 116 having a length $L_2$ which is greater than at least half the width or half the diameter $D_1$ of the substrates 106. Preferably, the length $L_2$ is greater than the width or the diameter $D_1$ of the substrates 106. By having array 114 of capacitive sensors 116 having a length $L_2$, fluid detector 102 is able to quickly scan the entire substrate 106 for fluid 110.

Sensor board 112 is preferably formed from a printed circuit board so as to allow the mounting of components, such as indicator 140, multiplexor 142, detection circuitry 150, substrate presence detector 160, substrate travel speed detector 166, and capacitive sensor 116, directly on to the sensor board 112. Referring to FIG. 7, in one embodiment, a rigid backing 115 is connected with the sensor board 112 in order to provide the sensor board 112 with additional rigidity. Preferably, the rigid backing 115 includes a rigid material such as metal, a fiber composite structure, or a rigid plastic.

Figure 15:
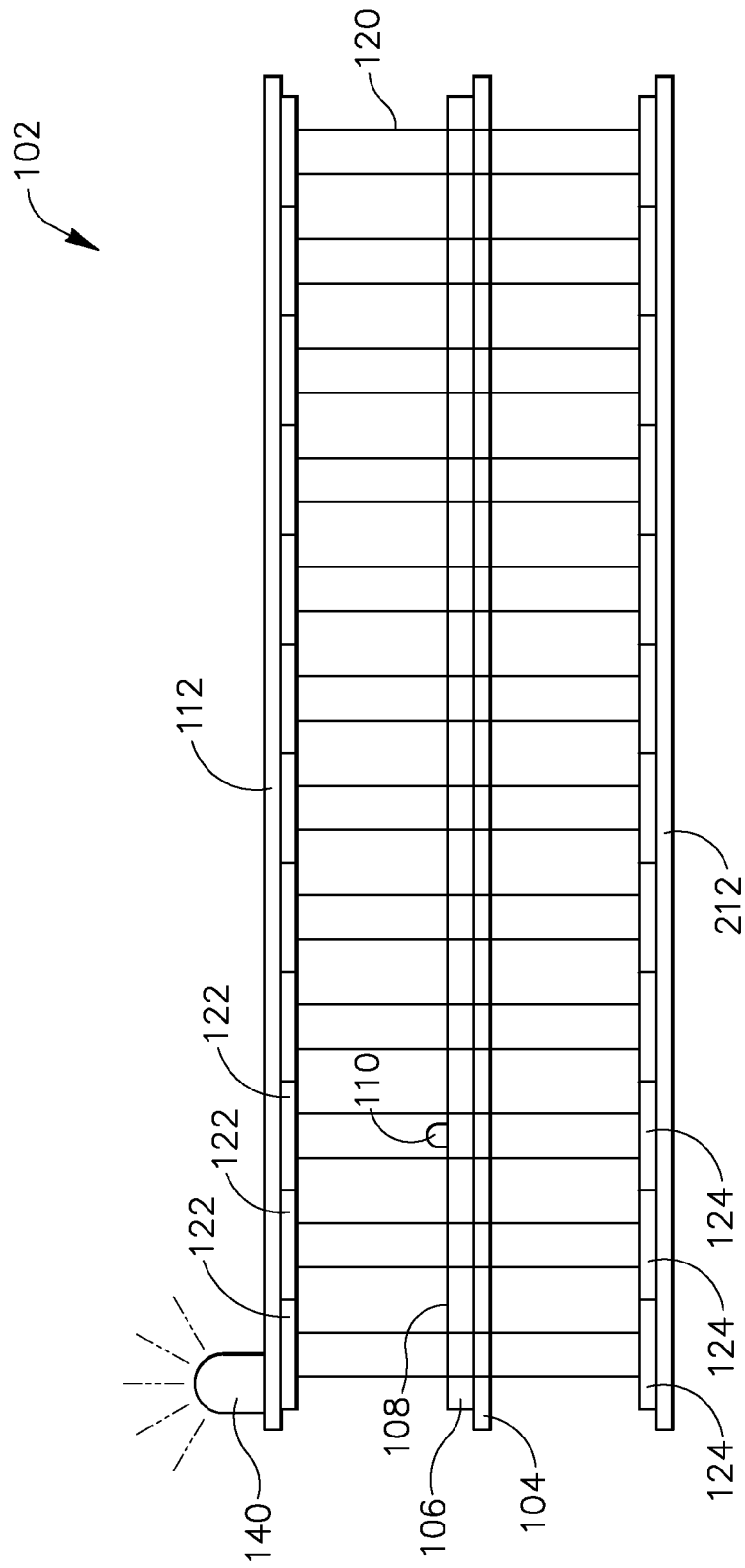
FIG. 15 depicts a cross-sectional view of a fluid detector, a platform, and a substrate from a system for detecting fluid on a substrate, in accordance with one embodiment of the present invention.

Referring to FIG. 2, in one embodiment, both the transmit sensor pad 122 and the receive sensor pad 124 are mounted on one side of the platform 104, both preferably a distance $d_1$ or less above the platform 104. The transmit and receive sensor pads 122 and 124 of each capacitive sensor 116 are preferably mounted on a bottom surface 128 of the sensor board 112 facing the platform 104. In this embodiment, the sensor pads 122 and 124 form a fringing electric field 120, where the electric field 120 bends and curves outwards from the transmit sensor pad 122 and then inwards to the receive sensor pad 124, as shown in FIG. 4. Forming a fringing electric field 120 has the advantage of keeping both pads 122 and 124 on the same side of the platform 104, simplifying the geometry of fluid detector 102. Additionally, by forming a fringing electric field 120, instead of a generally straight electric field 120, as shown in FIG. 15, the sensitivity of the capacitive sensor 116 is increased since the electric field 120 does not have to go through both the substrate 106 and the platform 104.

Preferably, the fringing electric field 120 extends a distance $d_2$ from the transmit and receive sensor pads 122 and 124, wherein the distance $d_2$ is greater than or equal to the distance $d_1$. Preferably the distance $d_2$ is at least 2 mm, more preferably the distance $d_2$ is at least 4 mm, and most preferably the distance $d_2$ is at least 5 mm. While the transmit and receive sensor pads 122 and 124 may be mounted on different planes, a distance apart from each other, mounting the transmit and receive sensor pads 122 and 124 on the same plane, side by side with each other, allows the transmit and receive sensor pads 122 and 124 to be both mounted on the same sensor board 112. Preferably, when mounting both the transmit sensor pad 122 and the receive sensor pad 124 on one side of platform 104, the pads 122 and 124 are mounted on a single sensor board 112, as shown in FIG. 2.

Referring to FIGS. 3 and 4, in one embodiment, when both the transmit sensor pad 122 and the receive sensor pad 124 are mounted on one side of the platform 104, a pad gap 130 is formed between the transmit sensor pad 122 and the receive sensor pad 124. Referring to FIG. 4, the pad gap 130 has a width $W_3$ of preferably less than 2 mm, more preferably a width $W_3$ of less than 1 mm, and most preferably a width $W_3$ of less than 0.5 mm.

Referring to FIG. 3, in one embodiment, when mounting both the transmit sensor pad 122 and the receive sensor pad 124 on one side of platform 104, the pad gap 130 is formed along a direction $d_p$ which is not parallel to or tangent to the direction of travel $d_t$. In this manner, by forming the pad gap 130 along a direction $d_p$ which is not parallel to or tangent to the direction of travel $d_t$, the sensitivity of the capacitive sensor 116 can be increased by increasing the probability that the droplet of fluid 110 will cross the pad gap 130 rather than travel parallel to the pad gap 130. Preferably, the transmit and receive sensor pads 122 and 124 form a parallelogram shape, with opposing angles which are not right angles, as shown in FIG. 3, so that the pad gap 130 is formed along a direction $d_p$ which is not parallel to or tangent to the direction of travel $d_t$.

Figure 16A:
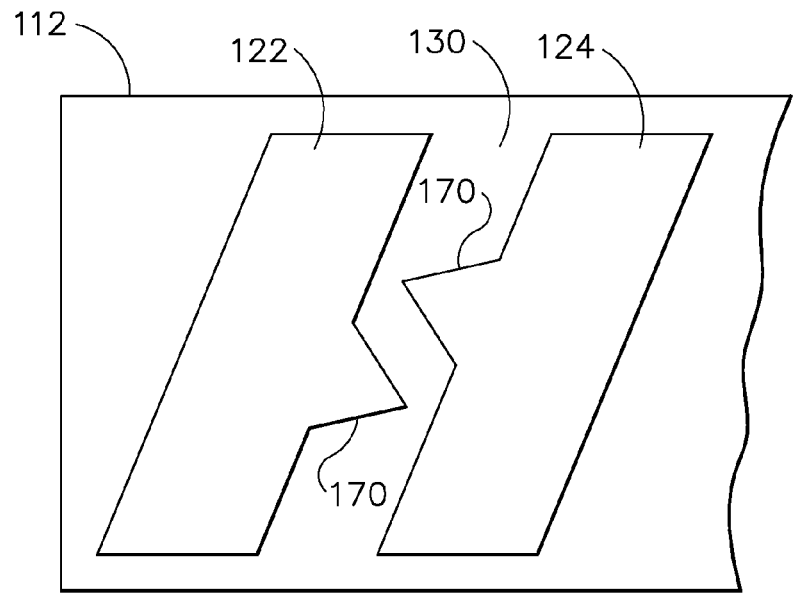
FIG. 16A depicts an enlarged partial bottom view of a fluid detector from a system for detecting fluid on a substrate, in accordance with one embodiment of the present invention.
Figure 16B:
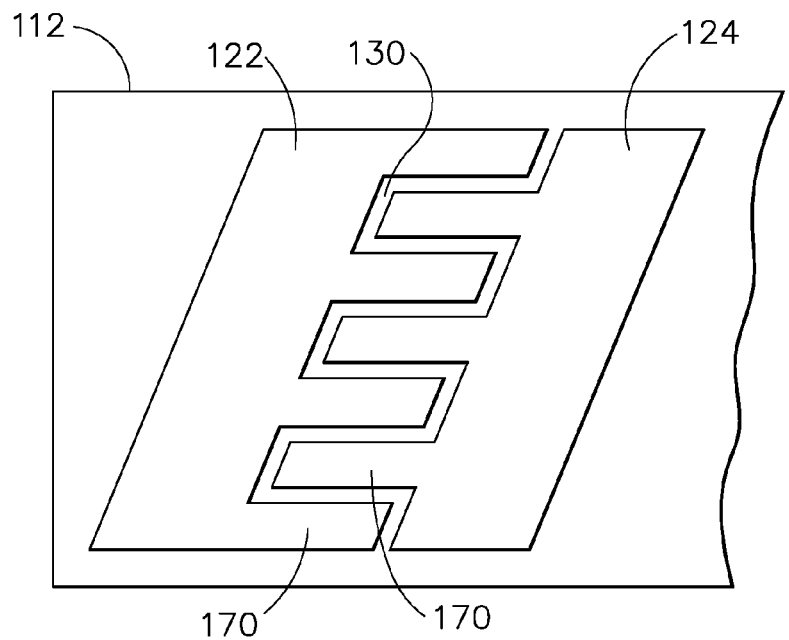
FIG. 16B depicts an enlarged partial bottom view of a fluid detector from a system for detecting fluid on a substrate, in accordance with one embodiment of the present invention.

Referring to FIGS. 16A and 16B, in one embodiment, the pad gap 130 forms a interdigitated finger pattern, in order to increase the sensitivity of the capacitive sensor 116. Preferably, both the transmit and receive sensor pads 122 and 124 form opposing fingers 170 which are interdigitated, as shown in FIGS. 16A and 16B to help increase the sensitivity of the capacitive sensor 116.

Referring to FIG. 15, in one embodiment, the transmit sensor pad 122 is mounted on a first side of the platform 104, and the receive sensor pad 124 is mounted on a second side of the platform 104 opposing the first side. In this embodiment, both sensor pads 122 and 124 are preferably mounted a distance $d_1$ or less above or below the platform 104. By mounting the sensor pads 122 and 124 both above and below the platform 104, the sensor pads 122 and 124 form a generally straight electric field 120 through both the platform 104 and the substrate 106. When mounting the transmit sensor pad 122 and the receive sensor pad 124 on opposite sides of platform 104, the pads 122 and 124 are preferably mounted on two sensor boards 112, 212 as shown in FIG. 15.

Referring to FIGS. 2, 3, and 4, at least one, and preferably, a plurality of capacitive sensors 116, and more specifically, a plurality of both transmit and receive sensor pads 122 and 124, are mounted to the sensor board 112. Preferably, an array 114 of capacitive sensors 116 made of transmit and receive sensor pads 122 and 124 is formed having a length $L_2$. The length $L_2$ is preferably greater than at least half the diameter $D_1$ of the substrate 106 and more preferably greater than or equal to the entire diameter $D_1$ of the substrate 106. In one embodiment, the array 114 has between 5 and 50 capacitive sensors 116, and more preferably between 5 and 20 capacitive sensors 116. In one embodiment, the array 114 has between 10 and 100 transmit and receive sensor pads 122 and 124, and more preferably between 10 and 40 transmit and receive sensor pads 122 and 124. In one embodiment, the array 114 comprises either transmit sensor pads 122 or receive sensor pads 124.

In operation, fluid detection system 100 detects fluid 110 on the surface 108 of substrate 106, as follows. First, a substrate 106 is placed onto the surface 105 of platform 104. The platform 104 is then moved, either rotationally via a rotational device 220, or linearly as in a conveyor system. The platform 104 in turn moves the substrate 106 under the capacitive sensor 116. The capacitance of the capacitive sensor 116 is measured and then a capacitance signal 121 is transmitted to the detection circuitry 150. In one embodiment, a substrate presence signal, along with a substrate travel speed signal, are separately transmitted to the detection circuitry 150 from a substrate presence detector 160 and a substrate travel speed detector 164, respectively. In one embodiment, information within the substrate presence signal and the substrate travel speed signal is instead extracted from just capacitance signal 121 alone. Upon receiving the capacitance signal 121, the detection circuitry 150 then determines if a substrate 106 is present or not, from either the capacitance signal 121 alone, or from a separate substrate presence signal.

If the detection circuitry 150 determines that a substrate 106 is present, the detection circuitry 150 then determines the speed of the substrate 106, from either the capacitance signal 121 alone, or from a separate substrate travel speed signal. Using the speed of substrate 106, the detection circuitry 150 then monitors the capacitance signal 121 for a substantial change or spike 180, as shown in FIGS. 9-12. A spike 180 represents a substantial change in the capacitance signal 121, which in turn indicates that a droplet of fluid 110 is present on the surface 108 of substrate 106. If detection circuitry 150 determines that a droplet of fluid 110 is present on the surface 108 of substrate 106, then a signal indicating that droplet of fluid 110 is present is then transmitted to indicator 140, and indicator 140 communicates this information to an end user by issuing an alert.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While various embodiments of the invention have been described, it will be apparent to those of ordinary skill in the art that other embodiments and implementations are possible within the scope of the invention. Accordingly, the invention is not to be restricted except in light of the attached claims and their equivalents.

The invention claimed is:

1. A system for detecting fluid on a substrate comprising:
    a sensor board;
    a first capacitive sensor mounted on the sensor board, the first capacitive sensor having a transmit sensor pad for transmitting a signal, a receive sensor pad for receiving the signal, and an analog-to-digital convertor connected with the receive sensor pad, wherein a pad gap is formed between the transmit sensor pad and the receive sensor pad, thereby forming an interdigitated finger pattern, and wherein the pad gap is less than 1 millimeter; and
    a platform upon which the substrate is to be placed, wherein the platform is a first distance from the transmit and receive sensor pads.

2. The system of claim 1, wherein the platform includes a mounting surface which is generally level with the ground.

3. The system of claim 1, wherein the platform includes a mounting surface upon which the substrate is to be placed, wherein the platform is connected with a rotational device for rotating the platform about a centralized axis normal with the mounting surface.

4. The system of claim 1, wherein the first distance is less than 10 mm.

5. The system of claim 1 further comprising a second capacitive sensor mounted on the sensor board adjacent the first capacitive sensor to form an array of capacitive sensors.

6. The system of claim 1, wherein the platform moves in a first direction with respect to the sensor board, wherein the pad gap is formed between the transmit sensor pad and the receive sensor pad along a second direction, and wherein the second direction of the pad gap is not parallel to or tangent to the first direction.

7. The system of claim 1, wherein the platform is a conveyor system.

8. A method for detection of fluid on a substrate comprising:
    placing the substrate on a platform under a fluid detector, wherein the fluid detector comprises a sensor board and a first capacitive sensor mounted on the sensor board, wherein the capacitive sensor includes a transmit sensor pad for transmitting a signal, and a receive sensor pad for receiving the signal, and wherein a pad gap is formed between the transmit sensor pad and the receive sensor pad, thereby forming an interdigitated finger pattern and wherein the pad gap is less than 1 millimeter;
    measuring a capacitance value between the transmit sensor pad and the receive sensor pad of the capacitive sensor; and
    determining if fluid is on the substrate based on the measured capacitance value.

9. The method of claim 8 further comprising moving the substrate under the fluid detector and measuring any change in the capacitance value while the substrate is being moved.

10. The method of claim 8 further comprising issuing an alert if it is determined that fluid is on the substrate.

11. The method of claim 8, wherein the first capacitive sensor further comprises an analog-to-digital convertor connected with the receive sensor pad.

12. The method of claim 8 further comprising moving the substrate in a rotational direction under the fluid detector.

13. An apparatus for detecting fluid on a substrate comprising:
    a first capacitive sensor positioned a distance away from a platform upon which the substrate is to be placed, the first capacitive sensor having a transmit sensor pad for transmitting a capacitance signal, a receive sensor pad for receiving the capacitance signal, and an analog-to-digital convertor connected with the receive sensor pad, wherein a pad gap is formed between the transmit sensor pad and the receive sensor pad, thereby forming an interdigitated finger pattern, wherein the pad gap is less than 1 millimeter, and wherein the capacitive sensor is capable of forming an electric field between the transmit sensor pad and the receive sensor pad when transmitting the capacitance signal, and wherein the electric field is capable of traveling to a surface of the substrate on the platform; and
    detection circuitry connected with the analog-to-digital convertor, comprising a microprocessor executing pattern recognition and decision making algorithms, wherein the detection circuitry is for analyzing any change in the capacitance signal by determining any change in the electric field and then determining if any fluid is present on the surface of the substrate on the platform.

14. The apparatus of claim 13, wherein both the transmit sensor pad and the receive sensor pad are mounted above the platform.

15. The apparatus of claim 13, wherein the first capacitive sensor is able to measure a change in the capacitance signal of 100 pico-Farads or less, with a resolution of five femto-Farads or less.

16. The apparatus of claim 13, wherein the first capacitive sensor is able to measure a change in the capacitance signal of 100 pico-Farads or less, with a resolution of five femto-Farads or less.

17. The apparatus of claim 13, wherein the first capacitive sensor generates a fringing field between the transmit sensor pad and the receive sensor pad when transmitting the capacitance signal.

18. The apparatus of claim 17, wherein the fringing field extends out at least 2 millimeters from either the transmit sensor pad or the receive sensor pad.

19. The apparatus of claim 13, further comprising a second capacitive sensor mounted on the sensor board adjacent to the first capacitive sensor to form an array of capacitive sensors.

20. The apparatus of claim 13, wherein an array of capacitive sensors is mounted on the sensor board, wherein a length of the array is 100 mm or more.

* * * * *